United States Patent
Ohashi et al.

(10) Patent No.: US 9,305,744 B2
(45) Date of Patent: Apr. 5, 2016

(54) MEASURING METHOD, DATA PROCESSING APPARATUS AND ELECTRON MICROSCOPE USING SAME

(71) Applicant: Hitachi High-Technologies Corporation, Minato-ku, Tokyo (JP)

(72) Inventors: Takeyoshi Ohashi, Tokyo (JP); Junichi Tanaka, Tokyo (JP); Tomoko Sekiguchi, Tokyo (JP); Hiroki Kawada, Tokyo (JP)

(73) Assignee: Hitachi High-Technologies Corporation, Tokyo (JP)

(\*) Notice: Subject to any disclaimer, the term of this patent is extended or adjusted under 35 U.S.C. 154(b) by 0 days.

(21) Appl. No.: 14/349,375

(22) PCT Filed: Sep. 27, 2012

(86) PCT No.: PCT/JP2012/074888
§ 371 (c)(1),
(2) Date: Apr. 3, 2014

(87) PCT Pub. No.: WO2013/051456
PCT Pub. Date: Apr. 11, 2013

(65) Prior Publication Data
US 2014/0246585 A1    Sep. 4, 2014

(30) Foreign Application Priority Data

Oct. 6, 2011  (JP) ................. 2011-221682

(51) Int. Cl.
*H01J 37/28* (2006.01)
*G01B 15/04* (2006.01)
*G01N 23/22* (2006.01)

(52) U.S. Cl.
CPC ................ *H01J 37/28* (2013.01); *G01B 15/04* (2013.01); *G01N 23/22* (2013.01); *G01B 2210/56* (2013.01); *H01J 2237/24578* (2013.01); *H01J 2237/2817* (2013.01)

(58) Field of Classification Search
USPC ........... 250/306, 307, 310, 311, 492.1, 492.2, 250/492.3
See application file for complete search history.

(56) References Cited

U.S. PATENT DOCUMENTS

| | | | |
|---|---|---|---|
| 2004/0051040 | A1 | 3/2004 | Nasu et al. |
| 2005/0247876 | A1 | 11/2005 | Kawada et al. |
| 2008/0130982 | A1 | 6/2008 | Kitamura et al. |
| 2012/0298865 | A1 | 11/2012 | Omori et al. |

FOREIGN PATENT DOCUMENTS

| | | |
|---|---|---|
| JP | 2005-338102 A | 12/2005 |
| JP | 2007-003535 A | 1/2007 |
| JP | 2008-164593 A | 7/2008 |
| JP | 2013-044547 A | 3/2013 |
| WO | WO 2011/089913 A1 | 7/2011 |

*Primary Examiner* — Nicole Ippolito
*Assistant Examiner* — Hanway Chang
(74) *Attorney, Agent, or Firm* — Miles & Stockbridge P.C.

(57) ABSTRACT

The objective of the invention is to provide a measuring method that can determine pattern contours and dimensions with high precision even if an object to be measured shrinks due to electron beam radiations. In order to achieve this objective, a method, which performs measurements by irradiating an electron beam onto a sample having a pattern formed on a primary coating thereof, prepares an SEM image and contour of the pattern (S201, S202), material parameters of the pattern part and primary coating part of the sample (S203, S204), and a beam condition in irradiating the electron beam onto the sample (S205), and uses these prepared things to calculate a pattern shape or dimensions before the irradiation of the electron beam (S206).

18 Claims, 14 Drawing Sheets

MEASURING METHOD, DATA PROCESSING APPARATUS AND ELECTRON MICROSCOPE USING SAME

TECHNICAL FIELD

The present invention relates to a measuring method for a fine pattern, a data processing apparatus and an electron microscope using same.

BACKGROUND ART

A lithography technology that an ArF excimer laser is used as a light source is used in fine pattern formation in a semiconductor manufacturing process. Since practical application of EUV (Extreme Ultraviolet Lithography) which is a next generation exposure light source of a shorter wavelength is delayed while pattern refining is being progressed, lithography near a resolution limit that a fine pattern of the size which is a fraction of a wavelength is formed using an ArF lithography technology comes to be performed. An OPC (Optical Proximity Correction) technology of correcting a mask pattern shape and an exposure light source shape by taking proximity effect of light into account is essential for the lithography near the resolution limit. For optimization of the OPC correction, it is necessary to modify a mask and a light source shape by measuring a sample (hereinafter, referred to as a fine resist sample or a resist sample) having a fine resist pattern created by actually transferring a mask pattern and evaluating a gap between it and design.

A scanning electron microscope (SEM) is used for measurement of the fine resist sample. However, when an ArF resist sample is to be measured by using the SEM, contraction (shrink) of the pattern of the resist sample caused by irradiation with an electron beam is generated and the dimension and the shape are changed. Therefore, in order to accurately measure the dimension and the shape of the pattern of the fine resist sample, it is necessary to accurately estimate shrinkage of the resist pattern and to correct it. In addition, since the resist sample is generally an insulator, there are cases where charging occurs on the sample surface caused by irradiation with the electron beam. In a case where charging occurs, the orbit of an incident electron beam is changed and some of signal electrons generated from the sample are brought back by positive charging of the sample surface, and an SEM image locally gets dark. As a result, there are cases where an error occurs in the dimension and the shape determined from the obtained SEM image. Accordingly, in order to accurately measure the pattern dimension and shape of the fine resist sample, it is necessary to also correct the error caused by charging.

As a method of estimating the shrinkage of the resist, the following method is indicated in Patent Literature 1. This is a method of estimating the shrinkage by measuring the resist sample a plurality of times by the SEM and obtaining a relation (a shrink curve) between a number of measurements and a change amount of the pattern dimension of the resist sample.

In addition, as a method of correcting the shrinkage in SEM observation of a two-dimensional pattern, the following method is indicated in Patent Literature 2. This is a method of adding a fixed value to a displacement amount of an edge position in the second and succeeding measurements such that an average value of the displacement amounts of edge points matches the first measurement in order to correct the influence of shrink in a case where measurement has been performed a plurality of times in measurement of a displacement in edge position between an acquired pattern shape and a reference shape.

In addition, as other methods, a method of correcting a contour by determining changes in dimension and shape due to shrink and an error due to charging by collating a database in accordance with a pattern shape of a sample, and a method of correcting a change in sample pattern position by calculating a stress between pattern parts of the sample are indicated in Patent Literature 3.

CITATION LIST

Patent Literature

PTL 1: Japanese Patent Application Laid-Open No. 2007-003535
PTL 2: Japanese Patent Application Laid-Open No. 2008-164593
PTL 3: WO 11/089,913

SUMMARY OF INVENTION

Technical Problem

In an optimization process for OPC correction, it is necessary to measure many resist samples having various pattern shapes and it is demanded to estimate an error caused by shrinkage and charging with precision for a resist sample of any pattern shape and to measure pre-shrinking dimension and contour. According to an experiment by inventors and others, it has been found that a change in shape due to shrink of the resist sample not only depends on resist material and shape but also is influenced by a primary coating material. Therefore, a method of estimating the shrinkage by taking the primary coating material into account is needed in order to estimate the shrinkage with precision. In addition, a method of correcting errors in dimension and contour caused by charging is needed.

In the method described in Patent Literature 1, it is possible to estimate the pre-shrinking dimension by performing a plurality of times of image acquisition to approximate dependency of the shrinkage on the number of measurements and storing an approximate. However, target patterns are limited to line patterns and hole patterns of fixed sizes and it cannot cope with a complicated two-dimensional shape. In addition, since the influence of the primary coating is not taken into account, it cannot accurately estimate the shrinkage for a pattern which is different in primary coating material.

In the method described in Patent Literature 2, an object to be corrected is the shrinkage in an interspace from the first measurement to the second and succeeding measurements and a method of deriving the pre-shrinking contour is not described. In addition, pattern shape dependency and primary coating dependency of the shrinkage are not taken into account and precise shrinkage estimation cannot be performed.

The method described in Patent Literature 3 makes it possible to estimate the shrinkage simply by performing one-time image acquisition by creating a database in advance and to estimate the shrinkage also including the pattern shape dependency of shrink. However, since the influence of the primary coating material is not taken into account, precise shrinkage estimation is difficult. Although a method of estimating the shrinkage by performing stress calculation is described as a method that the database is not created, the influence of the primary coating is not taken into account in stress calculation. In addition, although a method of performing correction by using a database which has been created in advance is described as a method of correcting the error caused by charging, there is such a drawback that time and labor are taken for constructing the database.

Therefore, in order to measure the pre-shrinking dimension and contour with precision, a shrinkage estimating method that the influence of the primary coating has been taken into account and a simple method of correcting the error caused by charging are needed.

An object of the present invention is to provide a measuring method, a data processing apparatus and an electron microscope using it, making it possible to obtain the pattern contour and dimension with high precision even in a case where an object to be measured shrinks by being irradiated with a charged particle beam such as an electron beam and so forth.

Solution to Problem

As one embodiment for attaining the above-mentioned object, a measuring method of irradiating a charged particle beam onto a sample that a pattern is formed on a primary coating using a material which is different from the material of the aforementioned primary coating, thereby measuring the aforementioned pattern has the step of preparing data including a pattern shape of the aforementioned sample acquired while the aforementioned charged particle beam is irradiating or after it has been irradiated onto the aforementioned sample, the step of preparing a parameter relating to shrink of a pattern part of the aforementioned sample, the step of preparing a parameter relating to shrink of a primary coating part of the aforementioned sample, the step of preparing a beam condition when irradiating the aforementioned charged particle beam onto the aforementioned sample and the step of calculating the pattern shape or dimension of the aforementioned sample before irradiating the aforementioned charged particle beam onto the aforementioned sample by using the data including the aforementioned pattern shape, the parameter relating to shrink of the aforementioned pattern part, the parameter relating to shrink of the aforementioned primary coating part and the aforementioned beam condition.

In addition, a data processing apparatus that processes data including shape information of a pattern of a sample that the pattern is formed on a primary coating using a material which is different from the material of the aforementioned primary coating is provided with a data saving means, a material parameter saving means and a shrink arithmetic operation unit, wherein the aforementioned image saving means is adapted to save image data that the aforementioned sample has been photographed, the aforementioned material parameter saving means is adapted to save a shrink parameter of a pattern part of the aforementioned sample and a shrink parameter of a primary coating part of the aforementioned sample, and the aforementioned shrink arithmetic operation unit is adapted to calculate a pattern shape before a charged particle beam is irradiated onto the aforementioned sample or a pattern shape after the charged particle beam has been irradiated onto the aforementioned sample by using the aforementioned image data, the shrink parameter of the aforementioned pattern part and the shrink parameter of the aforementioned primary coating part.

In addition, an electron microscope is provided with
the aforementioned data processing apparatus,
an electron source, an optical system adapted to irradiate an electron emitted from the aforementioned electron source onto the aforementioned sample, a detector that detects the electron emitted from the aforementioned sample and an apparatus control unit that controls them, wherein
the aforementioned data processing apparatus is adapted to calculate a pattern shape before an electron beam is irradiated onto the aforementioned sample or a pattern shape after the electron beam has been irradiated onto the aforementioned sample.

In addition, a measuring method of measuring a pattern of a sample that the pattern is formed on a primary coating using a material which is different from the material of the aforementioned primary coating has the step of preparing pattern data of the aforementioned sample before a charged particle beam is irradiated onto it, the step of preparing a parameter relating to shrink of the aforementioned sample pattern part, the step of preparing a parameter relating to shrink of the aforementioned sample primary coating part, the step of preparing a beam condition when measuring the pattern of the sample using the charged particle beam and the step of calculating a pattern shape or dimension obtained when measuring it by irradiating the charged particle beam of the aforementioned beam condition onto the aforementioned sample by using pattern data before the aforementioned charged particle beam is irradiated, the parameter relating to shrink of the aforementioned pattern part, the parameter relating to shrink of the aforementioned primary coating part, and the aforementioned beam condition.

Advantageous Effects of Invention

There can be provided the measuring method, the data processing apparatus and the electron microscope using the same allowing highly precise determination of the pattern contour and dimension even in a case where an object to be measured shrikes by being irradiated with the charged particle beam such as the electron beam and so forth.

DESCRIPTION OF EMBODIMENTS

As an embodiment for solving the above mentioned problems, an image processing method that image processing is performed on an SEM image acquired by a scanning electron microscope (an SEM) so as to perform shrink correction that the influence of a primary coating is taken into account and a correction method for an error caused by charging and a pre-shrinking pattern contour is output will be described.

Figure 1A:
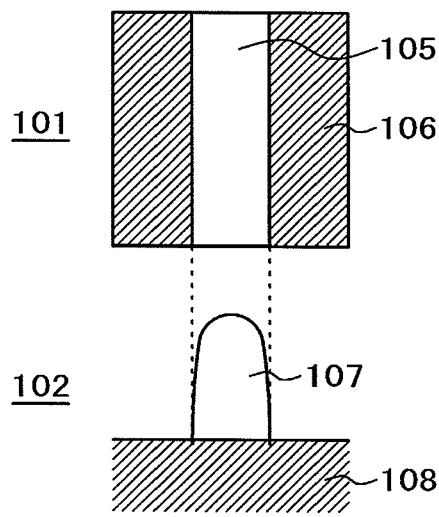
FIG. 1A is schematic diagrams of a sample pertaining to embodiments 1 to 7, in which an upper part shows a top plan view of the sample with a line pattern formed and a lower part shows a sectional diagram thereof.
Figure 1B:
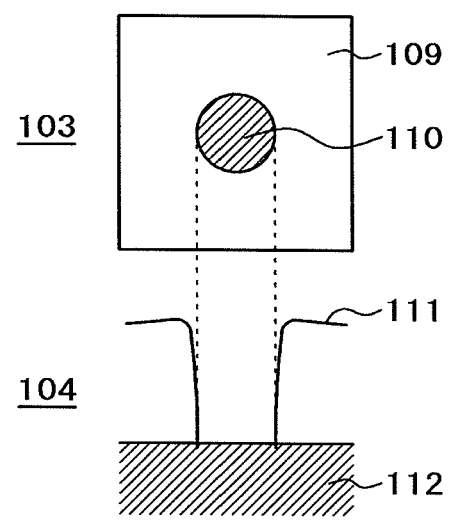
FIG. 1B is schematic diagrams of a sample pertaining to the embodiments 1 to 7, in which an upper part shows a top plan view of the sample with a hole pattern formed and a lower part shows a sectional diagram thereof.
Figure 1C:
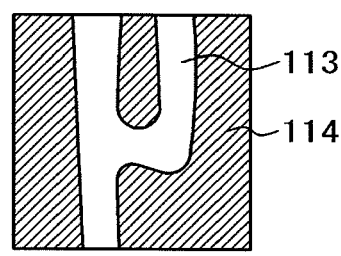
FIG. 1C is a schematic diagram of a sample pertaining to the embodiments 1 to 7, showing a top plan view thereof with an arbitrary pattern formed.
Figure 1D:
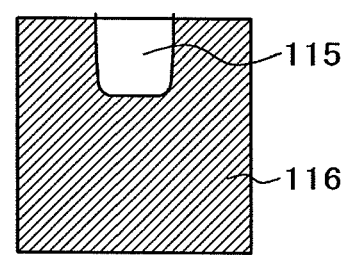
FIG. 1D is a schematic diagram of a sample pertaining to the embodiments 1 to 7, showing a sectional diagram thereof with an embedded pattern formed.

Here, the pattern means a convex-shape part formed on a sample surface and the primary coating means a part which is not a pattern when the sample is viewed from above. In addition, in a case where the material of the primary coating is also present under the pattern, it is also included in the primary coating. FIG. 1A and FIG. 1B show examples of the patterns and the primary coatings of line-shape and hole-shape samples. Reference numerals 101 and 103 denote schematic diagrams when the samples have been viewed from above and reference numerals 102 and 104 denote schematic diagrams of sections. In the case of the line-shape, regions 105 and 107 are the pattern parts and regions 106 and 108 are the primary coating parts, and in the case of the hole-shape, regions 109 and 111 are the pattern parts and regions 110 and 112 are the primary coating parts. The same thing also applies to such a general shape that, for example, a schematic diagram when the sample has been viewed from above is as shown in FIG. 1C not limited to the line shape and the hole shape. In a case where a region 113 is a convex part, the region 113 is the pattern part and a region 114 is the primary coating part. Further, though a sample surface is flat, in a sample which is made of two or more materials and has a structure that another material is embedded in a concave part of a certain material, a part 116 having a concave part is the primary coating part and an embedded part 115 is the pattern part as shown by a sectional diagram in FIG. 1D.

The patterns are, for example, various ArF resist patterns, and the primary coatings are, for example, an antireflection film, an oxide film, a nitrogen film, a silicon substrate and so forth.

In addition, the influence of the primary coating is an influence of stress that the primary coating part exerts on the pattern part and also includes an effect that the stress is changed with changing shrink and elastic modulus of the primary coating part by electron beam irradiation.

In addition, although in the later described embodiments, description will be made by taking image processing on the SEM image as an example, if it is the data including shape information of the sample, the same processing can be performed also on image data other than the SEM image and data which is not in an image format.

In the following, description will be made in detail with reference to embodiments.

Embodiment 1

A first embodiment pertaining to the present invention is an embodiment that a pre-shrinking pattern contour line is obtained from the SEM image.

Description will be made about the present embodiment using FIGS. 2 to 7.

Figure 2:
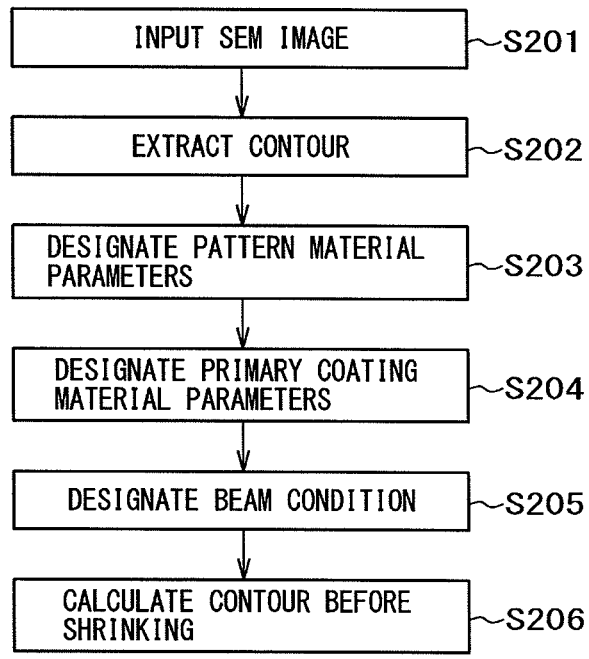
FIG. 2 is one example of a flowchart of image processing (pre-shrinking contour estimation) pertaining to the embodiment 1.

FIG. 2 is one example of a flowchart of image processing (pre-shrinking contour estimation) pertaining to the present embodiment.

Figure 3:
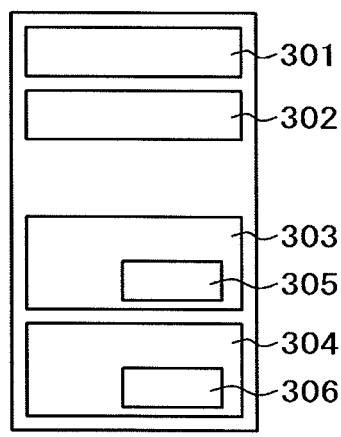
FIG. 3 is one example of a schematic general configuration diagram of an image processing apparatus pertaining to the embodiment 1.

FIG. 3 is one example of a schematic general configuration diagram of an image processing apparatus (a data processing apparatus) which is desirable when embodying this flowchart. The present apparatus is configured by an image saving unit 301, a material parameter saving unit 302, a contour extraction arithmetic operation unit 303 and a shrink arithmetic operation unit 304. The contour extraction arithmetic operation unit 303 and the shrink arithmetic operation unit 304 are respectively provided with memories 305 and 306 for saving data used in arithmetic operation. The aforementioned configuration may be implemented by configuring them as respectively independent devices or may be implemented by one or a plurality of computer(s). Incidentally, the same reference numerals denote the same constitutional elements.

In the following, description will be made along the flowchart in FIG. 2.

In step S201, an SEM image file that a resist sample to be measured has been photographed is input and saved into the image saving unit 301. It is desirable that the SEM image file be saved as a file of a format that information of the pattern part of the sample, information of the primary coating part and information of a beam condition of the SEM when acquiring the SEM image are included in conjunction other than image data detected with signal electrons of the SEM. The information of the pattern part and the primary coating part is the kinds and heights of their respective materials.

In addition, a file that these pieces of information are included may be prepared in association with the image file and may be input together with the image file even when these pieces of information are not included in the image file. In addition, an operator may be made to input it in later step as described later. Incidentally, the information and so forth of the pattern part and the primary coating part of the sample are saved into the parameter saving unit 302.

Figure 4:
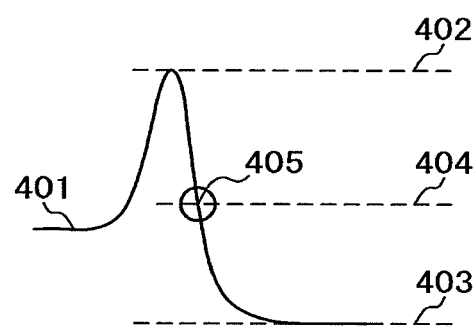
FIG. 4 is a schematic diagram for explaining a profile of image luminance in the embodiment 1.

In step S202, the SEM image data saved in the image saving unit 301 is stored into the memory 305 of the contour extraction arithmetic operation unit 303 and the contour of the sample is extracted by the contour extraction arithmetic operation unit 303 by using this data. The extracted contour data is stored into the memory 306 in the shrink arithmetic operation unit 304. Contour extraction is performed by extracting a pixel whose luminance is increased in the image. Further, as shown in FIG. 4, in the vicinity of the contour which has been extracted by the aforementioned method, a profile 401 that dependency of luminance on a position in a direction orthogonal to the contour line has been extracted may be created, an average luminance between a maximum value 402 of the luminance and a minimum value 403 of the luminance of the primary coating part may be obtained and the average luminance may be set as a reference value 404, and a position 405 where the luminance is set as the reference value may be extracted as a contour point. A value that the value of the maximum value 402 has been distributed to the value of the luminance 403 in the ratio which has been defined in advance may be set as the reference value, not limited to the average luminance.

Figure 5A:
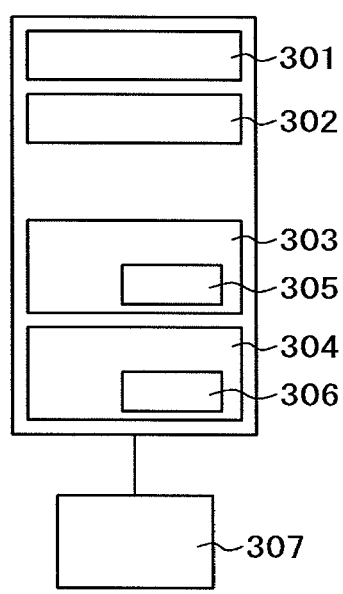
FIG. 5A is another example of the schematic general configuration diagram of the image processing apparatus pertaining to the embodiment 1.
Figure 5B:
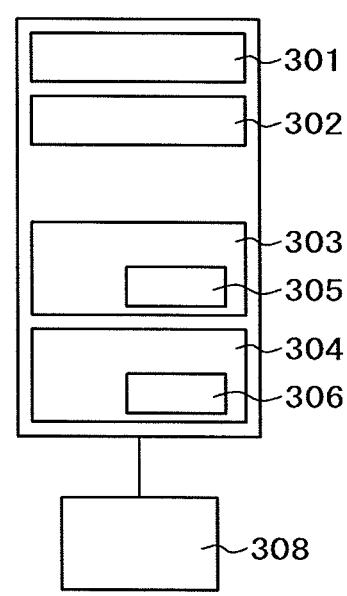
FIG. 5B is another example of the schematic general configuration diagram of the image processing apparatus pertaining to the embodiment 1.

In this case, when which side of left and right of a point that the luminance is maximized corresponds to the primary coating part is to be decided in FIG. 4, the side which is lower in luminance may be simply set as the primary coating, or the SEM image may be displayed on a monitor 307 which has been separately connected to the apparatus as shown in FIG. 5A so as to make the operator input which part corresponds to the primary coating or the pattern, or in a case where design data of a sample pattern to be measured is recorded in a database 308 which has been separately connected to the apparatus as shown in FIG. 5B, decision may be made with reference to this. Or, in a case where there exist a plurality of SEM images acquired for the same pattern, it is also possible to decide the pattern part and the primary coating part from a moving direction of the contour line. In this case, for the formerly acquired SEM image and the subsequently acquired SEM image, the aforementioned contours obtained by extracting the pixel whose luminance is increased in the image are compared to decide that the side whose contour line is moved is the pattern part. In this case, the precision can be improved by deciding the pattern part and the primary coating part depending on the moving direction of each contour point and setting the side which has been decided as the pattern part by the larger number of contour points as the pattern part. In a case where three or more SEM images are to be used, the precision can be further improved by deciding the pattern part by the aforementioned method with respect to a plurality of combinations of two SEM images such as the first and second ones, the first and third ones and so forth and setting a part which has been decided as the pattern part by the larger number of combinations as the pattern part. Incidentally, when comparing the plurality of images, pattern matching is performed by setting any one of the images as a reference image, a positional displacement of the pattern in the SEM image is measured, and after the pattern has been moved in the image so as to correct it, an error in image acquisition position which would occur for each imaged portion is corrected by performing comparison, by which more precise decision of the pattern part and the primary coating part can be performed.

In addition, an arbitrary method of extracting the contour from the image and an arbitrary method of discriminating the pattern from the primary coating part can be used.

Figure 6A:
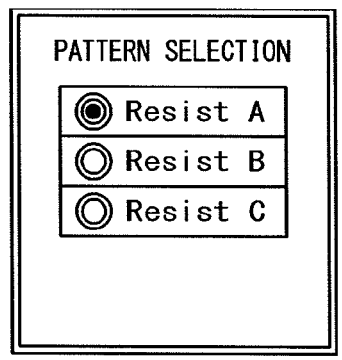
FIG. 6A is one example of a display image for input in the image processing apparatus pertaining to the embodiment 1.

In step S203, pattern material parameters, that is, a shrink parameter and a height of the pattern part are designated. Description will be made about the shrink parameter in step S206. In a case where information of the material and the height of the pattern is input together with the image data in step S201, the input information is extracted from within the shrink parameters of the various materials saved in the material parameter saving unit 302, and the shrink parameter of the material of the pattern part is stored into the memory 306 in the shrink arithmetic operation unit 304 in accordance with the input information and the height is stored into the memory 306 similarly. Incidentally, in this step, a display for inputting information of the pattern part as shown in FIG. 6A may be made on the monitor 307 which has been separately connected to the apparatus as shown in FIG. 5A so as to make the operator input the material and the height of the pattern part, instead of inputting the information of the pattern material together with the image data in step S201. Or, the operator may be made to directly input the shrink parameter without using the material parameter saving unit 302.

Figure 6B:
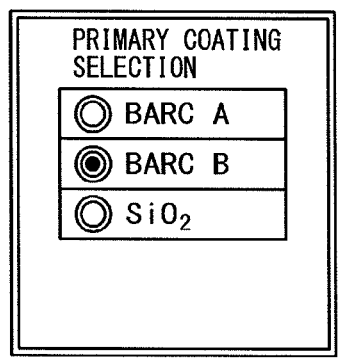
FIG. 6B is another example of the display image for input in the image processing apparatus pertaining to the embodiment 1.

In step S204, primary coating material parameters, that is, a shrink parameter and a height of the primary coating part are designated. The concrete method is the same as that in step S203. Incidentally, FIG. 6B is an example of a display when the operator is made to input them using the monitor 307.

Figure 6C:
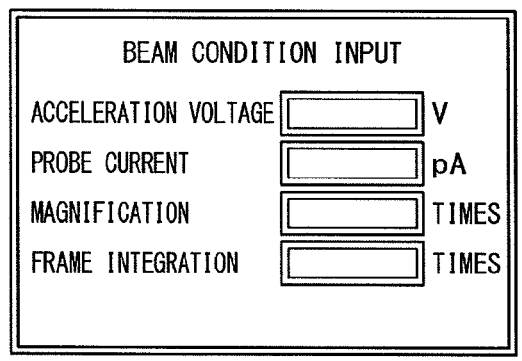
FIG. 6C is another example of the display image for input in the image processing apparatus pertaining to the embodiment 1.

In step S205, a beam condition of the SEM when acquiring the SEM image is designated. Here, the beam condition is, for example, an acceleration voltage of an incident electron, a probe current, a magnification of the SEM image, a number of repetitive scans (a number of frame integrations) or the like. It may be a scanning speed (a moving speed of the electron beam irradiation position when acquiring the SEM image), a number of pixels of the SEM image or the like as required and may be an electron beam irradiation amount per unit area. In a case where the beam condition has been input together with the image data in step S201, this is read into the memory 306 in the shrink arithmetic operation unit 304. Incidentally, since it is thought that the SEM image observes not the sample after the electron bean has been irradiated but the sample onto which the electron beam is being irradiated, it is desirable to read in not the total number of scans or electron beam irradiation amount used for image acquisition but a value which is smaller than that, for example, a halved value as the number of scans or the electron beam irradiation amount to the sample. In addition, a display for inputting the beam condition as shown in FIG. 6C may be made on the monitor 307 which has been separately connected to the apparatus as shown in FIG. 5A so as to make the operator input it in this step, instead of inputting the beam condition together with the image data in step S201.

In step S206, the pre-shrinking contour is calculated by using the contour data, the shrink parameter of the pattern part, the height of the pattern part, the shrink parameter of the primary coating part, the height of the primary coating part and the beam condition stored in the memory 306 in the shrink arithmetic operation unit 304 and is output. Although as an algorithm used in this arithmetic operation, if it is an algorithm that the pre-shrinking contour is estimated by taking the influence of the primary coating material into account, an arbitrary algorithm can be used, desirable examples will be described in the following.

One example is the method using elastic body simulation. In this algorithm, volume change moduli and elastic moduli relative to the electron beam irradiation amount are used as the shrink parameters of the pattern part and the primary coating part. First, mesh data of the sample shape including the primary coating is created from the contour data and the height data of the pattern and the primary coating. Next, the electron beam irradiation amount for each mesh is calculated from the beam condition data and a volume change due to shrink is obtained by using the volume change modulus relative to the electron beam irradiation amount per unit volume. In a case where a volume changed portion is to be restored, that is, it is tried to get it back to the volume before shrinking, an elastic energy generated in each mesh is calculated using the elastic modulus. Then, each mesh position is optimized such that the sum total of the elastic energies of the entire is minimized. The pattern contour after optimization is the pre-shrinking contour.

In addition, as another example, there is the method of using a rigid model. In this algorithm, as the material parameters, the volume change modulus relative to the electron beam irradiation amount and an integrating range of the shrinkages are used. Similarly to the aforementioned example, first, the mesh data of the sample shape including the primary coating is created. Next, the volume change due to shrink is calculated for each mesh to obtain a dimension change amount of the mesh. Thereafter, the dimension change amounts of the meshes included in the integrating range of the shrinkages are integrated to obtain an estimated shrinkage on each spot of the pattern and the estimated shrinkage is added to the contour data to obtain the pre-shrinking contour.

Further, since it is thought that in a case where a light intensity upon exposure is made different, the shrinkage generated relative to the same electron beam irradiation amount is made different regardless of the same resist pattern, in a case where it is possible to obtain a light intensity distribution upon exposure in the resist by a result of calculation by a lithography simulator, the voltage change modulus relative to the electron beam irradiation amount may be corrected in accordance with the light intensity in each mesh used in the above-mentioned example. When carrying out this, it is desirable to have a means for reading in the result of calculation by the lithography simulator by connecting a database that the result of calculation by the lithography simulator is saved and referring to this.

Figure 7A:
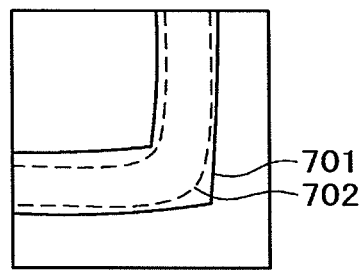
FIG. 7A is one example of a result display image in the image processing apparatus pertaining to the embodiment 1.
Figure 7B:
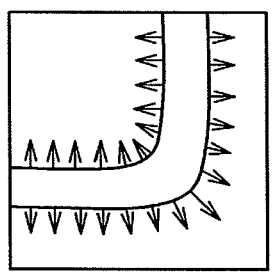
FIG. 7B is another example of the result display image in the image processing apparatus pertaining to the embodiment 1.
Figure 7C:
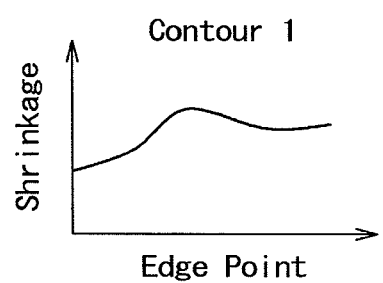
FIG. 7C is another example of the result display image in the image processing apparatus pertaining to the embodiment 1.

Incidentally, in a case where the monitor 307 is connected to the apparatus as shown in FIG. 5A, it is desirable to display the result of calculation. As an example of the display, a pre-shrinking contour 701 may be displayed together with a post-shrinking contour 702 as shown in FIG. 7A. Or, it may be displayed together with the SEM image. In addition, a shrink correction amount which is a difference between it and post-shrinking contour data, that is, an amount that the shrinkage has been positive-negative-inverted may be obtained and displayed on a vector together with the contour data as shown in FIG. 7B. In this displaying method, in a case where the shrink correction amount is small, it is desirable to extend the lengths of arrows at a constant rate so as to display them more visibly. Or, with respect to a specific contour line as shown in FIG. 7C, a distance of a certain contour point from an end of the contour line may be plotted on a horizontal axis and the shrinkage at that contour point may be plotted on a vertical axis. In this case, the vertical axis may be an absolute value of the shrinkage and only a component in a certain fixed direction such as a normal component of the contour line or the like may be displayed.

In addition, in a case where the obtained shrinkage exceeds a tolerance which has been defined in advance, the monitor 307 may be made to display a warning.

Although the above-mentioned method is one example of the method of estimating the pre-shrinking contour line with high precision from the SEM image, in the flow shown here, the step of storing the contour line data that another apparatus has output into the memory 306 in the shrink arithmetic operation unit 304 may be substituted for the process of obtaining the contour line data from the SEM image in step S201 and step S202. In this case, the contour extraction arithmetic operation unit 303 shown in the apparatus configuration diagram in FIG. 3 is not needed.

In addition, although the above-mentioned method can be applied to one SEM image, in order to perform more precise pre-shrinking contour estimation, the plurality of SEM images that the same portion has been imaged or the plurality of SEM images that different portions having patterns of similar shapes, for example, portions of the same pattern in different chips have been imaged may be used. This may be different portions on the same sample or on different samples. In a case where the plurality of SEM images are used, more precise pre-shrinking contour estimation becomes possible by taking an average of the pre-shrinking contours estimated from the respective images. In addition, the precision of the estimated pre-shrinking contour can be evaluated from a variation thereof. In a case where the SEM images of different portions are used, first, an image which takes an average of the respective images is created and the method of this embodiment may be applied to that averaged image. When averaging the images, although an average of the luminance of respective pixels may be simply taken, it becomes possible to obtain the more highly precise contour by performing pattern matching using any one of the images as a reference image, measuring a positional displacement of the pattern in the SEM image, moving the pattern in the image so as to correct it, and thereafter correcting an error in image acquiring position which would occur on each imaged portion by averaging the luminance of the respective pixels.

When the pattern contour is to be determined from the SEM image, highly precise shrink correction that the influence of the material of the primary coating has been taken into account can be made and it becomes possible to estimate the pre-shrinking contour line with high precision by using the above-mentioned method.

Embodiment 2

A second embodiment pertaining to the present invention is an embodiment that a pre-shrinking pattern dimension is determined from the SEM image. Incidentally, the matters described in the embodiment 1 and not described in the present embodiment can be also applied to the present embodiment unless there are special circumstances.

Description will be made about the present embodiment using FIGS. 8 and 9.

Figure 8:
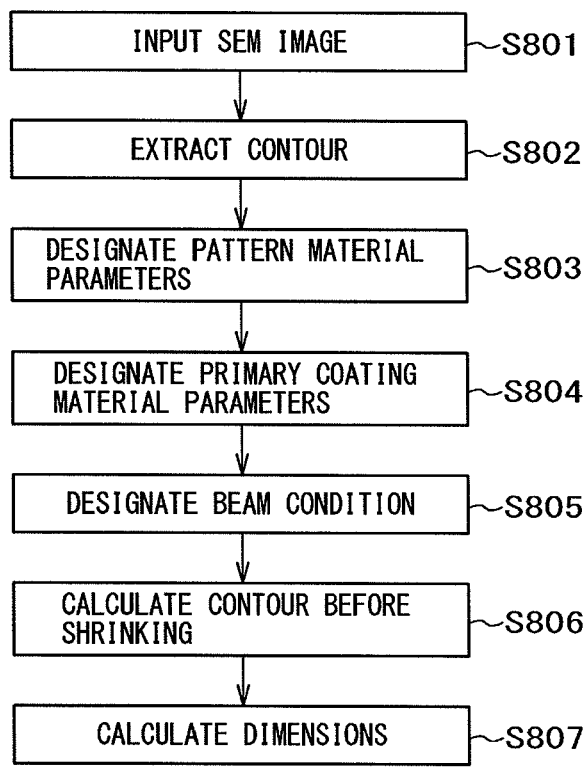
FIG. 8 is one example of a flowchart of image processing (pre-shrinking dimension estimation) pertaining to the embodiment 2.

FIG. 8 is one example of a flowchart of image processing pertaining to the present embodiment.

Figure 9:
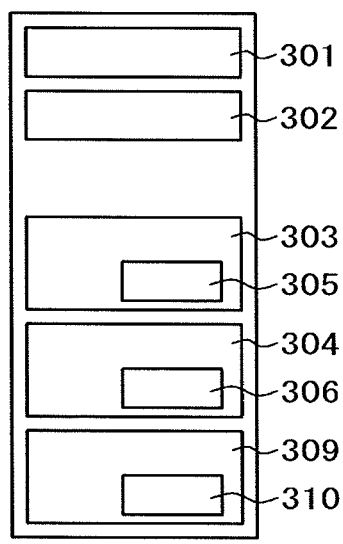
FIG. 9 is one example of a schematic general configuration diagram of an image processing apparatus pertaining to the embodiment 2.

FIG. 9 is one example of a schematic general configuration diagram of an image processing apparatus (a data processing apparatus) which is desirable when embodying the present embodiment. Constitutional elements which are duplications of those of the apparatus shown in FIG. 3 in the embodiment 1 are shown by using the same numbers and description thereof will be omitted. The present apparatus is configured by a dimension measurement arithmetic operation unit 309 provided with a memory 310 in addition to the constitutional elements in FIG. 3.

Description will be made along the flowchart in FIG. 8.

Steps S801 to S805 are the same as steps S201 to S205.

In step S806, although the pre-shrinking contour is calculated by the same method as that in step S206, this is stored into the memory 310 in the dimension measurement arithmetic operation unit 309, instead of outputting it.

In step S807, a distance between contour lines of predetermined parts of the pattern is obtained by the dimension measurement arithmetic operation unit 309 by using the pre-shrinking contour stored in the memory 310, statistical processing such as averaging or the like is performed as required and this is output as the dimension.

Although the above-mentioned method is one example of the method of estimating the pre-shrinking dimension with high precision from the SEM image, there are cases where a highly precise dimension value cannot be obtained depending on the contour extraction method used in step S802. In such a case, step S806 and step S807 may be replaced with a method which will be described in the following.

Although in step S806, the pre-shrinking contour is calculated by the same method as that in step S206, the shrinkage at each contour point, that is, a difference between the pre-shrinking contour and the post-shrinking contour is obtained and stored into the memory 310 in the dimension measurement arithmetic operation unit 309, instead of outputting this.

In step S807, the image data is read in from the image saving unit 301 and is stored into the memory 310 in the dimension measurement arithmetic operation unit 309. Next, a dimension value of a predetermined pattern part in the image data is obtained by the dimension measurement arithmetic operation unit 309. As an algorithm that the dimension is obtained from the SEM image, the well-known one may be used. Thereafter, the shrinkage of the pattern whose dimension is to be obtained is obtained from the shrinkages of the respective contour points stored in the memory 310. For example, in a case where the sample is of the line shape as shown in FIG. 1A, an average value of the shrinkages of the contour lines configuring the line may be obtained, and in a case where it is of the hole shape as shown in FIG. 1B, an average value of the shrinkages of the contour lines configuring the hole may be obtained. Then, the pre-shrinking dimension value is obtained by subtracting the shrinkage from the dimension value obtained from the SEM image and is output. However, in a case where the dimension to be obtained is the dimension of the primary coating part as in the case of the diameter of the hole shape, for example, in FIG. 1B, the pre-shrinking dimension value is obtained by adding the shrinkage to the dimension value obtained from the SEM image and is output.

Highly precise shrink correction that the influence of the material of the primary coating has been taken into account can be performed and the pre-shrinking dimension can be estimated with high precision by using the above-mentioned method when obtaining the dimension of the pattern from the SEM image.

Embodiment 3

A third embodiment pertaining to the present invention is an embodiment that a pattern contour line of the sample is obtained from the SEM image by performing correction of an error caused by charging. Incidentally, the matters described in the embodiment 1 or 2 and not described in the present embodiment can be also applied to the present embodiment unless there are special circumstances.

Description will be made about the present embodiment using FIGS. 10 to 12.

First, the error caused by charging will be described using FIG. 10.

Figure 10A:
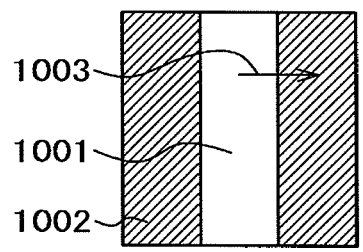
FIG. 10A is a schematic diagram for explaining a relation between a moving direction of an electron beam irradiation position and charging in the embodiment 3, showing a case where the moving direction thereof is orthogonal to a pattern contour line.
Figure 10B:
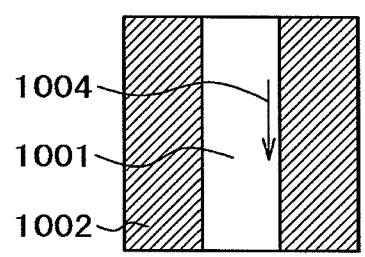
FIG. 10B is a schematic diagram for explaining a relation between the moving direction of the electron beam irradiation position and charging in the embodiment 3, showing a case where the moving direction thereof is parallel with the pattern contour line.

The image luminance may be sometimes reduced in the vicinity of the contour line in the SEM image obtained by moving the electron beam irradiation position in a direction which is nearly parallel with the orientation of the contour line in comparison with the SEM image acquired by moving the electron beam irradiation position in a direction which is nearly orthogonal to the orientation of the contour line when irradiating the electron beam onto the sample in order to acquire the SEM image. FIG. 10A and FIG. 10B schematically show the moving directions of the electron beam irradiation position in the respective cases by arrows 1003 and 1004 with respect to an contour line 1002 of a pattern part 1001 of the line shape, FIG. 10A shows a case of moving the electron beam irradiation position in a direction which is nearly vertical to the orientation of the contour line and FIG. 10B shows a case of moving it in a direction which is nearly parallel with it.

When the electron beam has been applied onto a contour part of the pattern, positive charging occurs on the sample as a result of emission of many signal electrons from the sample. This charging is attenuated by neutralization with the signal electrons generated by later electron beam irradiation, mitigation with time and so forth. However, in the case where the electron beam irradiation position is to be moved in the direction which is nearly parallel with the orientation of the contour line as shown in FIG. 10B, the electron beams are continuously irradiated onto the contour part of the pattern and large positive charging occurs. As a result, some of the signal electrons emitted from the sample by electron beam irradiation performed directly after that will be drawn back to the sample by positive charging on the sample. In that case, the brightness of the acquired SEM image is reduced on one side of the vicinity of the contour line.

Figure 11:
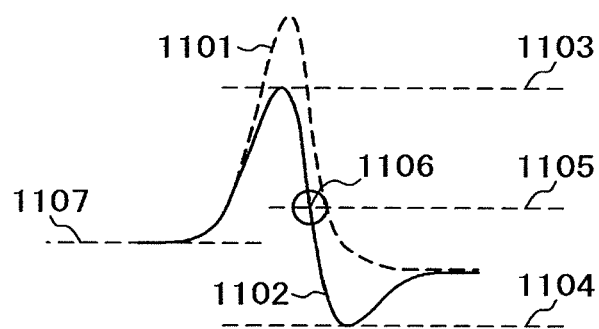
FIG. 11 is a schematic diagram for explaining the influence of charging on the profile of the image luminance in the embodiment 3.
Figure 12:
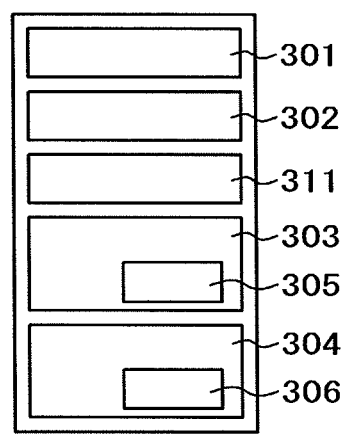
FIG. 12 is one example of a schematic general configuration diagram of an image processing apparatus pertaining to the embodiment 3.

FIG. 11 is a schematic diagram showing an example of a profile that dependency of the luminance on the position in the direction orthogonal to the contour line has been extracted with respect to the same position of the SEM image acquired by the methods shown in FIG. 10A and FIG. 10B. FIG. 10A and FIG. 10B respectively correspond to a dotted line 1101 and a solid line 1102. As shown by the solid line 1102, in a case where the electron beam irradiation position has been moved in the direction which is nearly parallel with the orientation of the contour line, luminance reduction occurs.

As described using FIG. 4 in the embodiment 1, a position 1106 of the contour point which is acquired by a method of obtaining the position of the contour point by obtaining a reference value 1105 from a maximum value 1103 of the profile of the image luminance and a minimum value 1104 thereof on the primary coating part for the profile 1102 in FIG. 11 is different from the original position acquired from the profile 1101. This is the error caused by charging.

Description will be made about the present embodiment that such an error is corrected using FIG. 2 and FIG. 12.

Although the flowchart of the present embodiment is the same as that in FIG. 2, as an algorithm for contour extraction in step S202, the one which will be described in the following is used. In addition, FIG. 12 is one example of a schematic general configuration diagram of an image processing apparatus (a data processing apparatus) which is desirable for embodying the present embodiment. The constitutional elements which are the duplications of those of the apparatus shown in FIG. 3 in the embodiment 1 are shown by using the same numbers and description thereof will be omitted. The present apparatus is configured by a charging correction data saving unit 331 in addition to the constitutional elements in FIG. 3.

In the algorithm of the present embodiment, as an index for indicating a change in profile by charging, an index A which indicates asymmetry of the profile is used. Assuming that R is a difference between the maximum value 1103 of the luminance and the minimum value 1104 of the luminance of the primary coating part and L is a difference between the maximum value 1103 of the luminance and a minimum value 1107 of the luminance of the pattern part, the index A will be given by the following formula.

$$A = L/(L+R)$$

If a relation between the index A and the error caused by charging is saved in advance in the charging correction data saving unit 311, the accurate contour point can be determined by obtaining the contour point by the method described in FIG. 4 when the contour point is to be obtained from the profile 1102, obtaining the index A and obtaining the error caused by charging with reference to the above-mentioned relation, and correcting this.

As a method of obtaining the relation between the index A and the error caused by charging, for example, profiles may be respectively obtained from the plurality of SEM images acquired under conditions which are different in the moving direction of the electron beam irradiation position relative to the contour line and the relation between the error caused by charging and the index A indicating the asymmetry may be obtained. In addition, the relation between the error caused by charging and the index A indicating the asymmetry may be also obtained by using the plurality of SEM images acquired under conditions which are different in moving speed of the electron beam irradiation position and in locus of the electron beam irradiation position. In this case, the original contour point position may be determined by using other means such as design data, a cross-sectional SEM, a cross-sectional TEM (Transmission Electron Microscope) and so forth and a displacement from this may be regarded as the error caused by charging, and assuming that there is no error caused by charging when the electron beam irradiation position has been moved in the direction orthogonal to the contour line, a displacement from this may be regarded as the error caused by charging.

The relation between the index A and the error caused by charging to be saved in the charging correction data saving unit 311 may be the one that the relation obtained by the aforementioned method is held in a table format or may be an approximate obtained by approximating a linear function, a quadratic function and so forth.

It becomes possible to estimate the contour of the pattern with high precision by correcting the error caused by charging when obtaining the dimension of the pattern from the SEM image, by using the above-mentioned method as the algorithm for contour extraction in step S202.

Embodiment 4

A fourth embodiment of the present invention is a SEM that the image processing apparatus shown in the embodiment 1 has been incorporated. Incidentally, the matters described in any one of the embodiments 1 to 3 and not described in the present embodiment can be also applied to the present embodiment unless there are special circumstances.

Description will be made about the present embodiment using FIG. 13.

Figure 13:
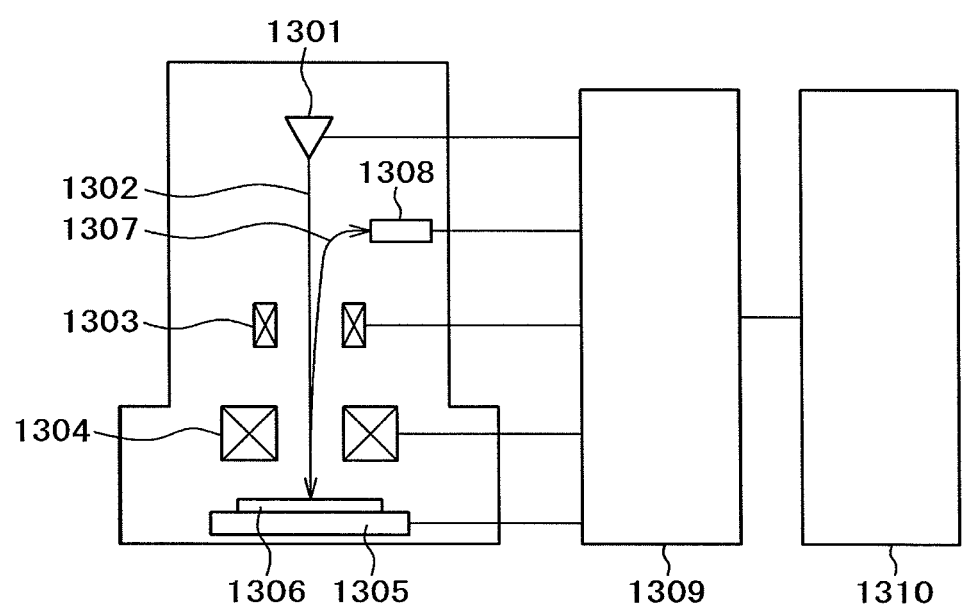
FIG. 13 is one example of the schematic general configuration diagram of an SEM pertaining to the embodiment 4.

FIG. 13 is one example of a schematic general configuration diagram of the SEM in the present embodiment, and an electron beam 1302 emitted from an electron source 1301 is deflected by a deflector 1303, is converged by an object lens 1304 and is irradiated onto a surface of a sample 1306 held on a stage 1305. A secondary electron 1307 emitted from the sample surface by being irradiated with the electron beam is detected by a detector 1308. These parts are controlled by an apparatus control unit 1309 and the SEM image is generated by indicating the intensity of a signal from the detector as the luminance of a pixel at a position on the image according to a deflection amount by the deflector. Contour correction is performed on this SEM image by using a contour correction arithmetic operation unit 1310. This contour correction arithmetic operation unit 1310 is the image processing apparatus shown in FIG. 3.

It becomes possible to acquire the pre-shrinking contour by applying the processing shown in the embodiment 1 to the image obtained by the SEM.

In addition, the pre-shrinking dimension may be made to be acquired by using the apparatus shown in the embodiment 2 as the contour correction arithmetic operation unit 1310.

Or, the contour that the error caused by charging has been corrected may be made to be acquired by using the apparatus shown in the embodiment 3 as the contour correction arithmetic operation unit 1310.

Embodiment 5

A fifth embodiment pertaining to the present invention is an embodiment that the shrinkage is calculated not from the SEM image but from the design data of the pattern and the post-shrinking contour, that is, the contour which will be obtained from the SEM image when the SEM image has been obtained by the SEM is estimated. Incidentally, the matters described in any one of the embodiments 1 to 4 and not described in the present embodiment can be also applied to the present embodiment unless there are special circumstances.

Description will be made about the present embodiment using FIGS. 14 and 15.

One example of a schematic general configuration diagram of an image processing apparatus which is desirable when embodying the present embodiment is the same as that in FIG. 3.

Figure 14:
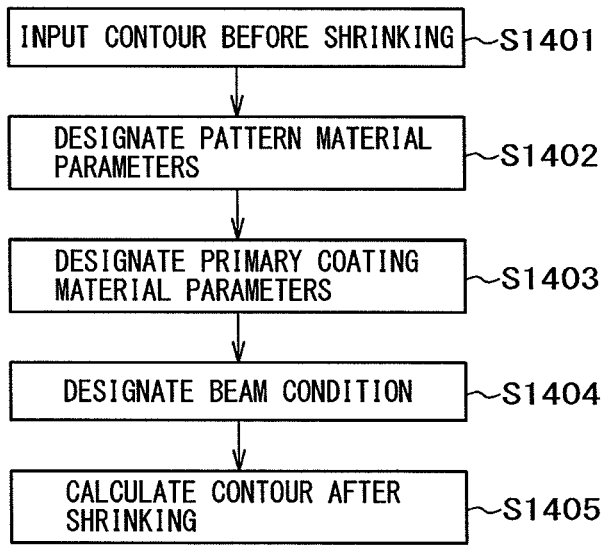
FIG. 14 is one example of a flowchart of image processing (post-shrinking contour estimation) pertaining to the embodiment 5.

FIG. 14 is one example of a flowchart of image processing (post-shrinking contour estimation) pertaining to the present embodiment.

In step S1401, the pre-shrinking contour of a resist sample whose post-shrinking contour is to be obtained is input and is stored into the memory 306 in the shrink arithmetic operation unit 304. The pre-shrinking contour may be either the contour data of the pattern part in design or the contour data of the pattern part obtained from an exposure anticipated result that the lithography simulator or the like outputs.

Steps S1402, S1403 and S1404 respectively similarly to steps S203, S204 and S205 designate the shrink parameter and the height of the pattern part, the shrink parameter and the height of the primary coating part and the beam condition and store them into the memory 306 in the shrink arithmetic operation unit 304. However, since SEM observation of the sample has not been actually performed, things to be input are a condition of an assumed sample and a condition for beam irradiation. It is desirable to input these pieces of information in conjunction by using a data format that information of the materials and the heights of the pattern part and the primary coating part is also included in a design data file when inputting the design data in step S1401. In addition, a file having the information of the materials and the heights of the pattern part and the primary coating part may be also input in association with the design data. In addition, the operator may be made to input it as described in the embodiment 1. In addition, a standard condition may be designated instead of designating the beam irradiation condition in step S1404.

In step S1405, the post-shrinking contour is calculated by using the contour data, the shrink parameter of the pattern part, the height of the pattern part, the shrink parameter of the primary coating part, the height of the primary coating part and the beam condition stored in the memory 306 in the shrink arithmetic operation unit 304 and is output. As an algorithm to be used in this arithmetic operation, if it is an algorithm that the post-shrinking contour is estimated by taking the influence of the primary coating material into account, an arbitrary algorithm can be used. Examples which are the same as the algorithm exemplified in the embodiment 1 will be described in the following.

One example is the method of using elastic body simulation. In this algorithm, the volume change moduli and elastic moduli relative to the electron beam irradiation amount are used as the shrink parameters of the pattern part and the primary coating part. First, the mesh data of the sample shape including the primary coating is created from the contour data and the height data of the pattern and the primary coating. Next, the electron beam irradiation amount for each mesh is calculated from the beam condition data and the volume change due to shrink is obtained by using the volume change modulus relative to the electron beam irradiation amount per unit volume. The elastic energy generated in each mesh as a result of occurrence of the volume change is calculated using the elastic modulus. Thereafter, each mesh position is optimized such that the sum total of the elastic energies of the entire is minimized. The pattern contour after optimization is the post-shrinking contour.

In addition, as another example, there is the method using the rigid model. In this algorithm, as the material parameters, the volume change modulus relative to the electron beam irradiation amount and the integrating range of the shrinkages are used. Similarly to the aforementioned example, first, the mesh data of the sample shape including the primary coating is created. Next, the volume change due to shrink is calculated for each mesh to obtain the dimension change amount of the mesh. Thereafter, the dimension change amounts of the meshes included in the integrating range of the shrinkages are integrated to obtain the estimated shrinkage on each spot of the pattern and the estimated shrinkage is subtracted from the contour data to obtain the post-shrinking contour.

Figure 15A:
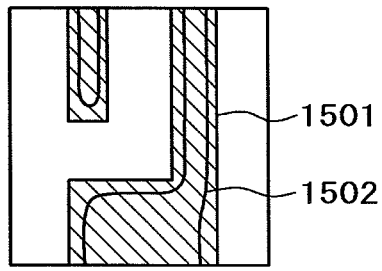
FIG. 15A is one example of a result display image in an image processing apparatus pertaining to the embodiment 5.
Figure 15B:
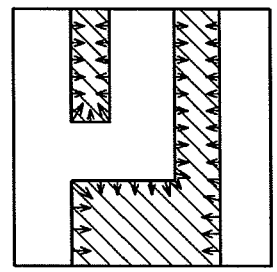
FIG. 15B is another example of the result display image in the image processing apparatus pertaining to the embodiment 5.
Figure 15C:
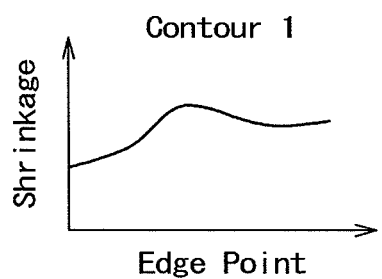
FIG. 15C is another example of the result display image in the image processing apparatus pertaining to the embodiment 5.

Incidentally, in a case where the monitor 307 is connected to the apparatus as shown in FIG. 5A, it is desirable to display a result of calculation. As an example of display, the pattern contour in design, or a pattern contour 1501 acquired from a result of output from the lithography simulator and a calculated post-shrinking contour 1502 may be displayed in conjunction as shown in FIG. 15A. In addition, the shrinkage which is the difference between it and the post-shrinking contour data may be obtained and displayed on the vector together with the contour data as shown in FIG. 15B. In this displaying method, in a case where the shrink correction amount is small, it is desirable to extend the lengths of arrows at a constant rate so as display them more visibly. Or, with respect to a specific contour line as shown in FIG. 15C, the distance of a certain contour point from the end of the contour line may be plotted on the horizontal axis and the shrinkage at that contour point may be plotted on the vertical axis. In this case, the vertical axis may be the absolute value of the shrinkage and only the component in the certain fixed direction such as the normal component of the contour line may be displayed.

In addition, in a case where the obtained shrinkage exceeds the tolerance which has been defined in advance, the monitor 307 may be made to display the warning. Further, a beam condition under which the shrinkage becomes not more than the tolerance may be searched and output.

It becomes possible to obtain the pattern contour and the shrinkage when acquiring the SEM image without actually acquiring the SEM image and it becomes possible to grasp and avoid in advance a risk of generation of a large shrink by using the above-mentioned method. In addition, in a case where image processing such as matching process or the like for obtaining the position of a specific pattern is to be performed on the acquired SEM image, since the accurate pattern shape can be estimated in advance, it becomes possible to construct a highly precise image processing algorithm.

Embodiment 6

A sixth embodiment pertaining to the present invention is an embodiment that a change in sectional shape due to shrink is estimated and corrected. Incidentally, the matters described in any one of the embodiments 1 to 5 and not described in the present embodiment can be also applied to the present embodiment unless there are special circumstances.

Figure 16:
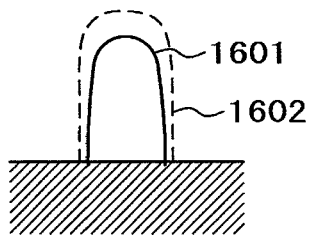
FIG. 16 is a schematic diagram for explaining pre- and post-shrinking pattern sectional shapes in the embodiment 6.

Description will be made about the present embodiment using FIG. 16.

This embodiment uses the sectional shape data as designated by the reference numerals 102 and 104 in FIG. 1 in place of the pattern contour data as designated by the reference numerals 101 and 103 in FIG. 1 and used in the embodiments 1 and 5. Accordingly, restoration of a pre-shrinking sectional shape from post-shrinking sectional shape data and estimation of a post-shrinking sectional shape from pre-shrinking sectional shape data become possible. FIG. 16 is a schematic diagram of the pre- and post-shrinking sectional shapes, in which a reference 1601 is the post-shrinking sectional shape and a reference numeral 1602 is the pre-shrinking sectional shape.

As the sectional shape data, an actual measurement result by the cross-sectional TEM, a cross-sectional STEM (Scanning Transmission Electron Microscope), the cross-sectional SEM, an AFM (Atomic Force Microscope) or the like may be used and a result of calculation by the lithography simulator or the like may be also used.

Incidentally, in the present embodiment, if the shrinkage is calculated by taking to what extent of damage due to the electron beam has been generated in which part of the sample into account by using simulation of scattering of incident electron beams in the sample and so forth, further more precise estimation will become possible.

Embodiment 7

A seventh embodiment pertaining to the present invention is an embodiment that when extracting the contour from the SEM image, an algorithm for contour extraction is modified by taking the change in sectional shape due to shrink into account. Incidentally, the matters described in any one of the embodiments 1 to 6 and not described in the present embodiment can be also applied to the present embodiment unless there are special circumstances.

Description will be made about the present embodiment using FIGS. 17 to 19.

Figure 17:
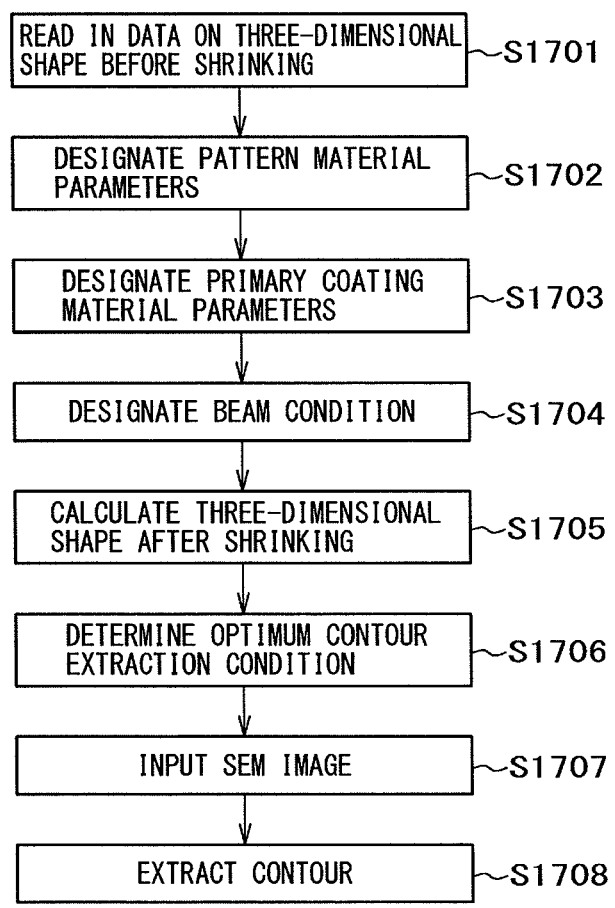
FIG. 17 is one example of a flowchart of image processing (post-shrinking contour estimation) pertaining to the embodiment 7.

FIG. 17 is a flowchart of information processing pertaining to the present embodiment.

Figure 18:
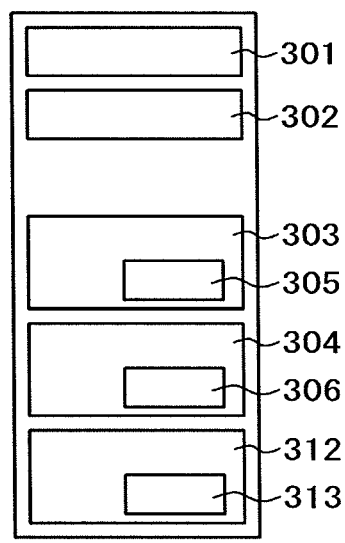
FIG. 18 is one example of a schematic general configuration diagram of the image processing apparatus pertaining to the embodiment 7.

FIG. 18 is one example of a schematic general configuration diagram of an image processing apparatus (a data processing apparatus) which is desirable when embodying this flowchart. The constitutional elements which are the duplications of those of the apparatus shown in FIG. 3 in the embodiment 1 are shown by using the same numbers and description thereof will be omitted. The present apparatus is configured by an optimum contour extraction condition arithmetic operation unit 312 provided with a memory 313 in addition to the constitutional elements in FIG. 3.

In the following, description will be made along the flowchart in FIG. 17.

In step S1701, pre-shrinking solid shape data of a sample to be measured is input and stored into the memory 306 in the shrink arithmetic operation unit 304. The solid shape data should be three-dimensional shape data of the sample to be SEM-observed and it is desirable to use a shape which is predicted by the lithography simulator. Or, it may be a solid shape which has been measured by using the AFM, the cross-sectional TEM, the cross-sectional SEM or the like and a solid shape which has been estimated by combining calculation with the actual measurement result.

Steps S1702, S1703 and S1703 are the same as steps S203, S204 and S205 described in the embodiment 1, or S1402, S1403 and S1404 described in the embodiment 5. However, since the heights of the pattern part and the primary coating part are included in solid shape data read in step S1701, they may not be designated in these steps.

In step S1705, a post-shrinking solid shape is calculated by using the pre-shrinking solid shape data, the shrink parameter of the pattern part, the shrink parameter of the primary coating part and the beam condition stored in the memory 306 in the shrink arithmetic operation unit 304 and is stored into the memory 313 in the optimum contour extraction arithmetic operation unit 312. Although as an algorithm used in this arithmetic operation, if it is an algorithm that the post-shrinking solid shape is estimated by taking the influence of the primary coating material into account, an arbitrary algorithm can be used, the examples which are the same as the algorithms exemplified in the embodiments 1 and 5 will be described in the following.

One example is the method of using elastic body simulation. In this algorithm, the volume change moduli and elastic moduli relative to the electron beam irradiation amount are used as the shrink parameters of the pattern part and the primary coating part. First, the mesh data of the sample shape including the primary coating is created from the solid shape data. Next, the electron beam irradiation amount for each mesh is calculated from the beam condition data and the volume change due to shrink is obtained by using the volume change modulus relative to the electron beam irradiation amount per unit volume. The elastic energy generated in each mesh as the result of occurrence of the volume change is calculated by using the elastic modulus. Thereafter, each mesh position is optimized such that the sum total of the elastic energies of the entire is minimized. The solid shape of the pattern after optimization is the post-shrinking solid shape.

In addition, as another example, there is the method using the rigid model. In this algorithm, as the material parameters, the volume change modulus relative to the electron beam irradiation amount and the integrating range of the shrinkages are used. Similarly to the aforementioned example, first, the mesh data of the sample shape including the primary coating is created. Next, the volume change due to shrink is calculated for each mesh to obtain the dimension change amount of each mesh. Thereafter, the dimension change amounts of the meshes included in the integrating range of the shrinkages are integrated to obtain the estimated shrinkage on each spot of the pattern and the estimated shrinkage is subtracted from the solid shape data to obtain the post-shrinking solid shape.

In step S1706, an optimum parameter upon contour extraction is determined by the optimum contour extraction condition arithmetic operation unit 312 by using the post-shrinking solid shape stored in the memory 313 and is stored into the memory 305 in the contour extraction arithmetic operation unit 303.

With respect to the method of determining the optimum parameter upon contour extraction, one example of that method will be described in the following.

Although in the generally used contour extracting method as described in FIG. 4, the position 405 where the luminance of the pixel becomes the luminance 404 of the reference value is detected as the contour point position, when the sectional shape of the pattern is made different, the height in the actual pattern at the contour point position which has been detected by this method is made different. That is, in a case where a level line of a fixed pattern height is to be obtained as the contour line, the correct contour line cannot be obtained by the aforementioned method.

Figure 19:
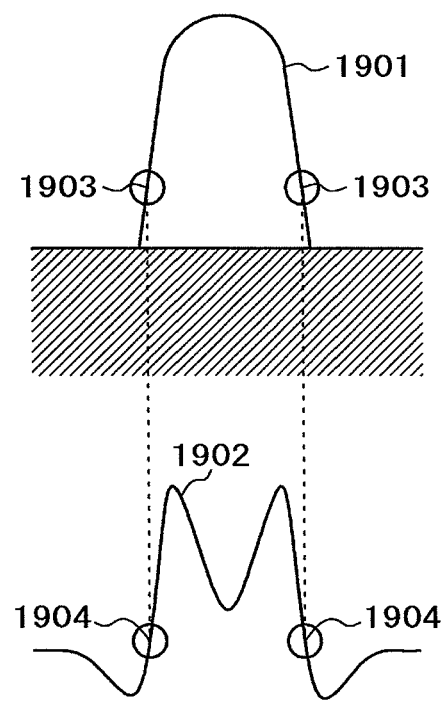
FIG. 19 is a schematic diagram for explaining a correspondence between a sectional shape and a profile of image luminance in the embodiment 7.

In the present step, a sectional shape 1901 of a portion that contour point extraction is performed is obtained from the post-shrinking solid shape stored in the memory 313, an intensity distribution of signal electrons in a case where the SEM image has been acquired for that sectional shape is calculated by using scattering simulation and so forth of the electron beams to estimate a profile 1902 of the luminance of the image as shown in FIG. 19. Accordingly, a position 1904 which corresponds to a position 1903 of the height that the contour line is to be measured in the actual pattern and is on the profile of the luminance can be found. Such a distribution rate of the minimum value to the maximum value of the luminance of the primary coating part that the luminance at that position is set as the reference value is an optimum contour extraction condition. The optimum contour extraction condition like this is determined for each portion that the contour is measured.

In step S1707, SEM image data that a sample to be measured has been photographed is input and is stored into the memory 305 of the contour extraction arithmetic operation unit 303.

Figure 20:
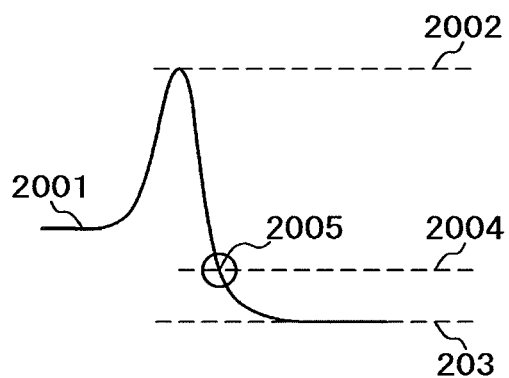
FIG. 20 is a schematic diagram for explaining the profile of the image luminance in the embodiment 7.

In step S1708, the contour of the sample is extracted by the contour extraction arithmetic operation unit 303 by using the optimum contour extraction condition and the SEM image data stored in the memory 305 and is output. FIG. 20 is an example of a case where a value at which the optimum contour extraction condition is 20:80, that is, the distribution rate of a value of a maximum value 2002 to a value of a minimum value 2003 of the luminance of the primary coating part of a luminance profile 2001 is 20:80 becomes the reference value, and in this case, a position 2005 becoming a luminance reference value 2004 is detected as the position of the contour point. The contour of a pattern height position to be obtained can be extracted at each measurement portion by using the same method.

Contour extraction that cross-section deformation due to shrink is also taken into account becomes possible by the above-mentioned method and it becomes possible to obtain the contour line at a desired pattern height.

Incidentally, the contour line obtained by this method is the post-shrinking contour line and it becomes possible to obtain the pre-shrinking contour line with high precision by embodying the embodiments 1 and 2 uninterruptedly.

Embodiment 8

An eighth embodiment pertaining to the present invention is an embodiment that the material parameter used in the embodiments 1 to 7 is obtained. In this embodiment, the shrinkages are actually measured for the plurality of patterns and the material parameter is adjusted so as to obtain a value which matches actual measurement in shrinkage estimation. Incidentally, the matters described in any one of the embodiments 1 to 7 and not described in the present embodiment can be also applied to the present embodiment unless there are special circumstances.

Although as the plurality of patterns, for example, patterns of the line shape and the hole shape which are different in line width, or the line shape and the hole shape that they are arranged in different cycles are desirable for precise parameter determination, it is also applicable with respect to patterns of a plurality of arbitrary shapes.

Description will be made about the present embodiment using FIGS. 21 and 22.

Figure 21:
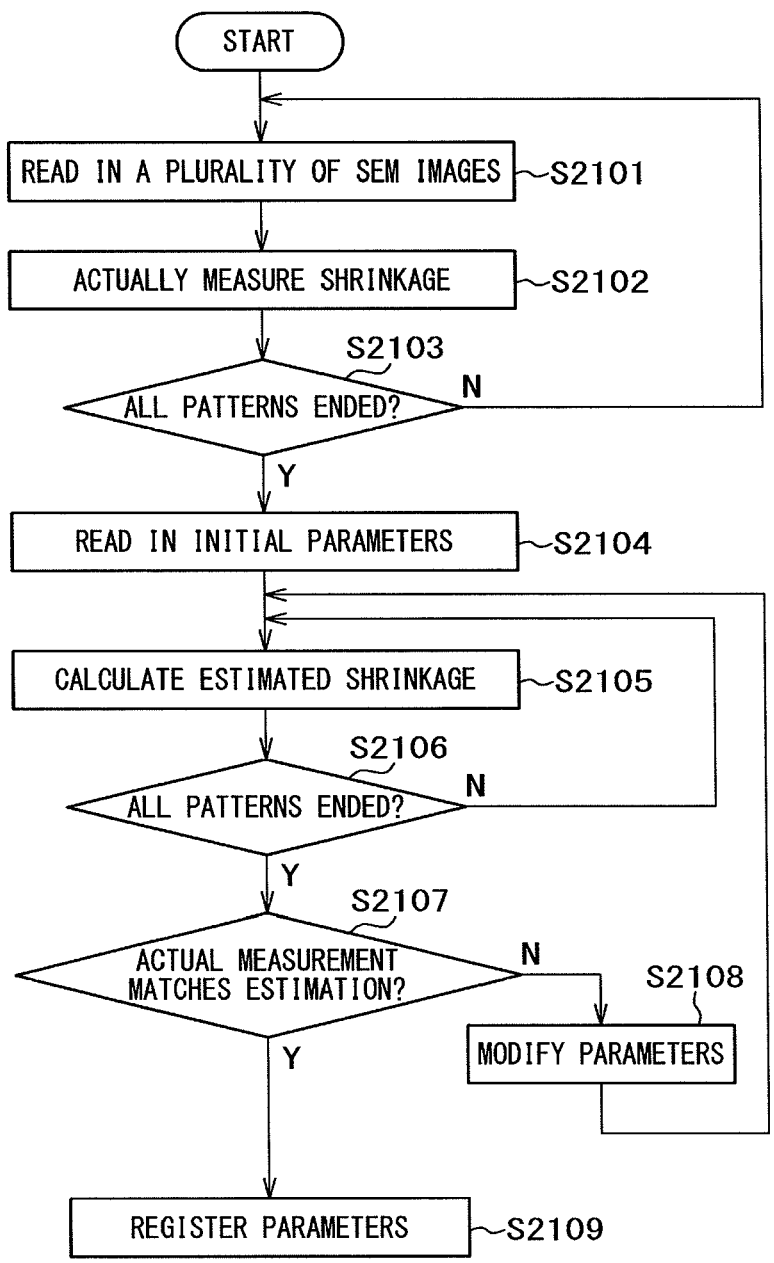
FIG. 21 is one example of a flowchart of information processing (adjustment and registration of material parameters) pertaining to the embodiment 8.

FIG. 21 is a flowchart of information processing (adjustment and registration of the material parameter) pertaining to the present embodiment.

Figure 22:
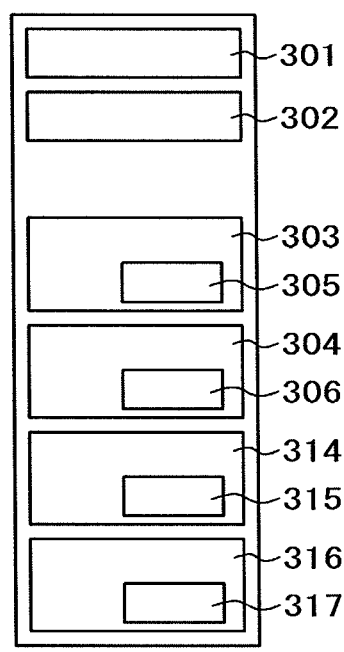
FIG. 22 is one example of a schematic general configuration diagram of an image processing apparatus pertaining to the embodiment 8.

FIG. 22 is one example of a schematic general configuration diagram of an image processing apparatus (a data processing apparatus) which is desirable when embodying this flowchart. The constitutional elements which are the duplications of those of the apparatus shown in FIG. 3 in the embodiment 1 are shown by using the same numbers and description thereof will be omitted. The present apparatus is configured by a shrink measurement arithmetic operation unit 314 provided with a memory 315 and a shrink comparison arithmetic operation unit 316 provided with a memory 317 in addition to the constitutional elements in FIG. 3.

In the following, description will be made along the flowchart in FIG. 21.

In step S2101, the plurality of SEM images which have been continuously imaged are read in with respect to the same portion of the pattern made of the material whose material parameter is to be determined, are saved in the image saving unit 301 and are stored into the memory 315 of the shrink measurement arithmetic operation unit 314. Incidentally, for more precise parameter determination, it is desirable to reduce the electron beam irradiation amount when acquiring one SEM image. In addition, the precision can be further improved by imaging different portions having patterns of similar shapes and using an SEM image which has been averaged among them.

In step S2102, the SEM images stored in the memory 315 are mutually compared by the shrink measurement arithmetic operation unit 314, the shrinkage is measured and an obtained shrinkage actually measured value is stored into the memory 317 of the shrink comparison arithmetic operation unit 316. Although, as a shrink measuring method, if it is an algorithm that pieces of measurement data before and after shrinking are compared to calculate the shrinkage of the pattern, an arbitrary method can be applied, for example, there are methods described in the following. There are the method of measuring a space between the contour lines before and after shrinking with respect to each contour point by extracting the contour lines and the method of obtaining a change amount of the dimension value in the case of the line pattern and the hole pattern. In addition, in a case where three or more SEM images are to be used, a method of approximating a relation between a number of times of image pickup-up and the beam irradiation amount, and a shrinkage change amount may be used.

In step S2103, with respect to all of the SEM images that patterns of various shapes which have been set in advance have been imaged, whether shrinkage actual measurement has been terminated or not is decided, and when not terminated, it returns to step S2101.

In step S2104, initial parameters are stored into the memory 306 in the shrink arithmetic operation unit 304 as the shrink parameters of the material and the primary coating. The initial parameter may be a fixed value which has been set in advance or in a case where the monitor 307 is connected as shown in FIG. 5A, an input screen may be displayed on this so as to make the operator input it. Or, in a case where it can be estimated from the shrinkage acquired in step S2102, an estimated value thereof may be used.

In step S2105, the shrinkage is estimated for one of the SEM images saved in the image saving unit 301 and a shrink estimated value is stored into the memory 317 of the shrink comparison arithmetic operation unit 316. A concrete shrinkage estimating method will be described in the following.

First, step S202 of the embodiment 1 is executed on the target SEM image to calculate the contour data and it is stored into the memory 306 in the shrink arithmetic operation unit 304. In addition, the heights of the pattern part and the primary coating part and the beam condition are designated and stored into the memory 306. This may be performed by the same method as the method described in steps S203, S204 and S205 of the embodiment 1. However, with respect to the beam condition, the difference in beam condition between the SEM images so compared in step S2102 is designated. For example, in a case where the compared images are the first SEM image and the second SEM image that the same place has been imaged continuously, the difference between them, that is, the beam condition for the amount that one SEM image is acquired is designated.

Thereafter, the pre-shrinking contour is calculated by using the contour data, the shrink parameter of the pattern part, the height of the pattern part, the shrink parameter of the primary coating part, the height of the primary coating part and the beam condition and the shrinkage at each contour point is obtained from a difference between it and the post-shrinking contour data.

Or, in a case where the shrinkage has been measured from the change amount of the dimension value in step S2102, with respect to each of the calculated pre-shrinking contour and the post-shrinking contour, the dimension value is obtained by using the method and so forth described in step S807 of the embodiment 2 and a difference between them is set as the shrinkage.

In step S2106, with respect to all of the SEM images that the patterns of various shapes which have been set in advance have been imaged, whether shrinkage estimation has been terminated or not is decided, and when not terminated, it returns to step S2105.

In step S2107, the shrink actually measured value stored in the memory 317 and the shrink estimated value are mutually compared with respect to all of the patterns of various shapes which have been set in advance by using the shrink comparison arithmetic operation unit 316, and when an error is not more than a threshold value which has been set in advance, it proceeds to step S2109 and when it exceeds the threshold value, it proceeds to step S2108. Here, as the error, an average value of the errors at the respective contour points of the respective patterns may be used or a value obtained by other statistical processing may be used.

In step S2108, the shrink parameter is modified. As an algorithm for modification, an existing method such as a Newton's method or the like may be used.

In step S2109, the obtained shrink parameter is recorded into the material parameter saving unit 302.

The material parameter used in the embodiments 1 to 7 can be determined by the method described above.

Incidentally, the parameters of both of the pattern material and the primary material may be determined by the above-mentioned method, or with respect to one of the parameters, the already registered one may be used and the remaining other parameter may be newly determined.

Incidentally, the present invention is not limited to the above-mentioned embodiments and various modified examples are included. For example, the above-mentioned embodiments have been described in detail in order to explain the present invention intelligibly and they are not always limited to those provided with all of the described configurations. In addition, it is also possible to replace part of one embodiment with the configuration of another embodiment. In addition, it is also possible to add the configuration of another embodiment to the configuration of a certain embodiment. In addition, with respect to part of the configuration of each embodiment, addition, deletion and replacement of another configuration are possible.

REFERENCE SIGNS LIST

101 . . . schematic diagram of line-shape sample when viewed from above, 102 . . . schematic diagram of section of line-shape sample, 103 . . . schematic diagram of hole-shape sample when viewed from above, 104 . . . schematic diagram of section of hole-shape sample, 105 . . . pattern part, 106 . . . primary coating part, 107 . . . pattern part, 108 . . . primary coating part, 109 . . . pattern part, 110 . . . primary coating part, 111 . . . pattern part, 112 . . . primary coating part, 113 . . . pattern part, 114 . . . primary coating part, 115 . . . pattern part, 116 . . . primary coating part, 301 . . . image saving unit, 302 . . . material parameter saving unit, 303 . . . contour extraction arithmetic operation unit, 304 . . . shrink arithmetic operation unit, 305 . . . memory of contour extraction arithmetic operation unit, 306 . . . memory of shrink arithmetic operation unit, 307 . . . monitor, 308 . . . database of design data, 309 . . . dimension measurement arithmetic operation unit, 310 . . . memory of dimension measurement arithmetic operation unit, 311 . . . charging correction data saving unit, 312: optimum contour extraction condition arithmetic operation unit, 313 . . . memory of optimum contour extraction condition arithmetic operation unit, 314 . . . shrink measurement arithmetic operation unit, 315 . . . memory of shrink measurement arithmetic operation unit, 316 . . . shrink comparison arithmetic operation unit, 317 . . . memory of shrink comparison arithmetic operation unit, 401 . . . luminance profile, 402 . . . maximum value of luminance, 403 . . . minimum value of luminance of primary coating part, 404 . . . reference value of luminance, 405 . . . contour detection position, 701 . . . pre-shrinking contour, 702 . . . past-shrinking contour, 1001 . . . pattern part, 1002 . . . contour line, 1003 . . . moving direction of electron beam irradiation position, 1004 . . . moving direction of electron beam irradiation position, 1101 . . . luminance profile not influenced by charging, 1102 . . . luminance profile influenced by charging, 1103 . . . maximum value of luminance, 1104 . . . minimum value of luminance of primary coating part, 1105 . . . reference value of luminance, 1106 . . . contour detection position, 1107 . . . minimum value of luminance of pattern part, 1301 . . . electron source, 1302 . . . electron beam, 1303 . . . deflector, 1304 . . . object lens, 1305 . . . stage, 1306 . . . sample, 1307 . . . secondary electron, 1308 . . . detector, 1309 . . . apparatus control unit, 1310 . . . contour correction arithmetic operation unit, 1501 . . . pattern contour and so forth in design, 1502 . . . post-shrinking contour, 1601 . . . post-shrinking sectional shape, 1602 . . . pre-shrinking sectional shape, 1901 . . . sectional shape, 1902 . . . estimated luminance profile, 1903 . . . position corresponding to contour line measured height of sectional shape, 1904 . . . position corresponding to contour line measured height of luminance profile, 2001 . . . luminance profile, 2002 . . . maximum value of luminance, 2003 . . . minimum value of luminance of primary coating part, 2004 . . . reference value of luminance, 2005 . . . contour detection position.

The invention claimed is:

1. A method of measuring a pattern formed on a sample including a wafer and a primary coating layer formed on the wafer, by irradiating a charged particle beam onto the sample, the pattern being formed on the primary coating layer using a material which is different from the material of the primary coating layer so that the primary coating layer is positioned between the pattern and the wafer, the method comprising:
   a step of preparing data including a pattern shape of the sample acquired while the charged particle beam is irradiating or after it has been irradiated onto the sample;
   a step of preparing a parameter relating to shrink of a pattern part of the sample;
   a step of preparing a parameter relating to shrink of a primary coating layer part of the sample;
   a step of preparing a beam condition when irradiating the charged particle beam onto the sample, and
   a step of calculating the pattern shape or dimension of the sample before irradiating the charged particle beam onto the sample by using the data including the pattern shape, the parameter relating to shrink of the pattern part, the parameter relating to shrink of the primary coating layer part, and the beam condition.

2. The measuring method according to claim 1,
wherein the pattern is a pattern formed by a resist, and
the pattern shape or dimension of the sample before irradiating the charged particle beam onto the sample is a pre-shrinking shape or dimension of the pattern.

3. The measuring method according to claim 2, further comprising:
a step of displaying shrinkage of the pattern.

4. The measuring method according to claim 3, further comprising:
a step of deciding whether the shrinkage of the pattern exceeds a prescribed value or not.

5. The measuring method according to claim 1, wherein the steps of preparing the parameters relating to shrinks of the pattern part and the primary coating layer part utilize a database which saves shrink parameters of a plurality of materials.

6. The measuring method according to claim 1, wherein the data including the pattern shape of the sample acquired while the charged particle beam is irradiating or after it has been irradiated onto the sample is an electron microscope image acquired using an electron microscope for the sample or contour line data extracted from the electron microscope image.

7. The measuring method according to claim 1, wherein the pattern shape is a sectional shape of the pattern.

8. The measuring method according to claim 1, wherein the step of preparing the data including the pattern shape of the sample includes a step of correcting an error in the pattern shape or dimension caused by charging of the sample.

9. The measuring method according to claim 8, wherein, in the step of correcting the error in shape or dimension caused by charging of the sample, an algorithm utilizing asymmetry of a profile of image luminance is used.

10. The measuring method according to claim 1, wherein the parameter relating to shrink of the pattern part and the parameter relating to shrink of the primary coating layer part are parameters determined from shrinkages of a plurality of line patterns which are different in line width.

11. A data processing apparatus that processes data including information of a shape of a pattern formed on a sample including a wafer and a primary coating layer formed on the wafer, the pattern being formed on the primary coating layer using a material which is different from the material of the primary coating, so that the primary coating layer is positioned between the pattern and the wafer, comprising:
a data saving means;
a material parameter saving means; and
a shrink arithmetic operation unit,
wherein the image saving means is adapted to save image data that the sample has been photographed,
the material parameter saving means is adapted to save a shrink parameter of a pattern part of the sample and a shrink parameter of a primary coating layer part of the sample, and
the shrink arithmetic operation unit is adapted to calculate a pattern shape before a charged particle beam is irradiated onto the sample or a pattern shape after the charged particle beam has been irradiated onto the sample by using the image data, the shrink parameter of the pattern part, and the shrink parameter of the primary coating layer part.

12. An electron microscope, comprising:
the data processing apparatus according to claim 11;
an electron source;
an optical system adapted to irradiate an electron emitted from the electron source onto the sample;
a detector that detects the electron emitted from the sample; and
an apparatus control unit that controls them,
wherein the data processing apparatus is adapted to calculate a pattern shape before an electron beam is irradiated onto the sample or a pattern shape after the electron beam has been irradiated onto the sample.

13. The electron microscope according to claim 12,
wherein the image data is image data of the electron microscope acquired by observing the sample through an electron beam microscope,
the data processing apparatus further has a means for extracting contour data from the image data of the electron microscope, and
the shrink arithmetic operation unit is adapted to calculate a pattern shape before observation through the electron microscope by using the contour data in place of the image data.

14. A method of measuring a pattern formed on a sample including a wafer and a primary coating layer formed on the wafer, the pattern being formed on the primary coating layer using a material different from the material of the primary coating layer so that the primary coating layer is positioned between the pattern and the wafer, comprising:
a step of preparing pattern data of the sample before a charged particle beam is irradiated onto it;
a step of preparing a parameter relating to shrink of a pattern part of the sample;
a step of preparing a parameter relating to shrink of a primary coating layer part of the sample;
a step of preparing a beam condition when measuring the pattern of the sample by using the charged particle beam, and
a step of calculating a pattern shape or dimension obtained when measuring it by irradiating the charged particle beam of the beam condition onto the sample by using the pattern data before the charged particle beam is irradiated, the parameter relating to shrink of the pattern part, the parameter relating to shrink of the primary coating layer part, and the beam condition.

15. The measuring method according to claim 14, further comprising:
a step of displaying shrinkage of the pattern generated when measuring it by irradiating the charged particle beam of the beam condition onto the sample.

16. The measuring method according to claim 14, further comprising:
a step of searching for the beam condition such that shrinkage of the pattern generated when measuring it by irradiating the charged particle beam of the beam condition onto the sample becomes not more than a prescribed value.

17. The measuring method according to claim 14, wherein the pattern data is data of a sectional shape of the pattern.

18. The measuring method according to claim 14,
wherein the pattern shape obtained when measuring it by irradiating the charged particle beam of the beam condition onto the sample is a solid shape of the pattern, and comprising:
a step of inputting an electron microscope image acquired by using an electron microscope for the sample, and
a step of extracting the shape of the pattern from the electron microscope image by utilizing the solid shape of the pattern.

* * * * *